(12) United States Patent (10) Patent No.: US 9,165,334 B2
Simon (45) Date of Patent: Oct. 20, 2015

(54) PET AND PEOPLE CARE MANAGEMENT SYSTEM

(75) Inventor: Doug Simon, Chicago, IL (US)

(73) Assignee: Pet Check Technology LLC, Chicago, IL (US)

( * ) Notice: Subject to any disclaimer, the term of this patent is extended or adjusted under 35 U.S.C. 154(b) by 10 days.

(21) Appl. No.: 13/338,021

(22) Filed: Dec. 27, 2011

(65) Prior Publication Data

US 2012/0166322 A1 Jun. 28, 2012

Related U.S. Application Data

(60) Provisional application No. 61/427,779, filed on Dec. 28, 2010.

(51) Int. Cl.
*G06Q 10/00* (2012.01)
*G06Q 50/22* (2012.01)

(52) U.S. Cl.
CPC ..................................... *G06Q 50/22* (2013.01)

(58) Field of Classification Search
CPC ................................................. G06Q 30/0261
See application file for complete search history.

(56) References Cited

U.S. PATENT DOCUMENTS

| | | | |
|---|---|---|---|
| 5,288,980 A * | 2/1994 | Patel et al. | 235/381 |
| 6,243,039 B1 * | 6/2001 | Elliot | 342/457 |
| 6,331,825 B1 * | 12/2001 | Ladner et al. | 340/988 |
| 6,618,593 B1 * | 9/2003 | Drutman et al. | 455/456.3 |
| 6,788,200 B1 * | 9/2004 | Jamel et al. | 340/539.13 |
| 7,789,802 B2 * | 9/2010 | Lee et al. | 482/8 |
| 8,285,611 B2 * | 10/2012 | Fuller et al. | 705/34 |
| 8,320,931 B2 * | 11/2012 | Ward et al. | 455/456.1 |
| 8,538,458 B2 * | 9/2013 | Haney | 455/456.2 |
| 8,626,120 B2 * | 1/2014 | Amora et al. | 455/407 |
| 2001/0026240 A1 * | 10/2001 | Neher | 342/357.07 |
| 2002/0169583 A1 * | 11/2002 | Gutta et al. | 702/188 |
| 2006/0053447 A1 * | 3/2006 | Krzyzanowski et al. | 725/40 |
| 2006/0099969 A1 * | 5/2006 | Staton et al. | 455/456.4 |
| 2006/0201432 A1 * | 9/2006 | Pratt | 119/51.02 |
| 2006/0223518 A1 * | 10/2006 | Haney | 455/420 |
| 2007/0198180 A1 * | 8/2007 | Sakamoto | 701/211 |
| 2008/0027591 A1 * | 1/2008 | Lenser et al. | 701/2 |
| 2008/0146251 A1 * | 6/2008 | Meadows et al. | 455/456.5 |
| 2008/0186166 A1 * | 8/2008 | Zhou et al. | 340/539.13 |
| 2008/0284591 A1 * | 11/2008 | Armstrong et al. | 340/540 |
| 2009/0289844 A1 * | 11/2009 | Palsgrove et al. | 342/357.07 |
| 2010/0030590 A1 * | 2/2010 | Sodaro | 705/5 |
| 2010/0331145 A1 * | 12/2010 | Lakovic et al. | 482/8 |

(Continued)

OTHER PUBLICATIONS

BettaWalka (2008). From appointments to invoices, getting paid with BettaWalka Pro.*

(Continued)

*Primary Examiner* — Peter L Ludwig
(74) *Attorney, Agent, or Firm* — Hinshaw & Culbertson LLP

(57) ABSTRACT

A pet or human care management system and method are provided. In one embodiment, the system includes a portable electronic device carried by a care service provider to scan a care customer bar code at the location of a care visit to indicate the start and/or end of the care visit. The portable electronic device also includes a GPS component and transmits its location at a plurality of times during the care visit, such as to indicate the path of a scheduled walk. A website is employed to administrate the care management system, including scheduling walks, licensing care providers, and creating customer and care provider accounts.

4 Claims, 6 Drawing Sheets

(56) References Cited

U.S. PATENT DOCUMENTS

| | | | | |
|---|---|---|---|---|
| 2011/0197157 | A1* | 8/2011 | Hoffman et al. | 715/772 |
| 2012/0009943 | A1* | 1/2012 | Greenberg | 455/456.1 |
| 2012/0011216 | A1* | 1/2012 | Zuber | 709/206 |
| 2012/0095812 | A1* | 4/2012 | Stefik et al. | 705/13 |
| 2012/0130794 | A1* | 5/2012 | Strieder | 705/14.27 |
| 2012/0143031 | A1* | 6/2012 | Belalcazar et al. | 600/377 |
| 2012/0190386 | A1* | 7/2012 | Anderson | 455/456.3 |
| 2012/0226472 | A1* | 9/2012 | Yuen et al. | 702/160 |
| 2012/0290217 | A1* | 11/2012 | Shoval et al. | 702/19 |
| 2012/0290312 | A1* | 11/2012 | Maruoka | 705/2 |
| 2013/0124227 | A1* | 5/2013 | Ellis | 705/3 |

OTHER PUBLICATIONS

Veriwalk (Nov. 4, 2011). Live GPS dog tracking software.*
The Retrieva Portable Tracker (Apr. 18, 2010).*
Jawad, S. et al. (2009). A multipurpose child tracking system design and implementation. Int'l Journal of Soft Computing Applications 4, pp. 57-68.*
Pet Check Technology (Sep. 25, 2011). Created by dog walkers for dog walkers.*
Fancy Pups (Jan. 9, 2013). Keep Constant Track of Your Pet With the Dog GPS.*
Animalsmile (Feb. 2, 2010). Dog Tracking Systems Brands & Reviews.*
Ungerleider, N. (Jun. 5, 012). Dog owners, watch your pooch being walked (and much more) with this iPhone App.*
123Pet Software (Sep. 14, 2010). Dog and Car Grooming Software that's easy to use.*
Pouge, D. (Apr. 23, 2009). State of the Art: Zoombak tracks your dog, your car, even your children. NY Times, p. B1 of the New York Edition. Retrieved on Jan. 30, 2013 from: http://www.nytimes.com/2009/04/23/technology/personaltech/23pogue.html?pagewanted=all (hereinafter "Zoombak").*
Showalter, Tom (Aug. 17, 2010). Foursquare Check Out. Presentation on "SlideShare" (hereinafter "Foursquare").*
Buttner, S. et al. (Sep. 2010). Exploring physical check-ins for location-based services. UbiComp '10. Copenhagen, Denmark.*
@RyanTaft (2010). How to use Foursquare to grow your business . . . Catalyst Marketers.*
The examiner defines "to record" (verb) as "to cause to be set down or registered: to record one's vote." See Random House Dictionary, 2014.*
Pouge, D. (Apr. 23, 2009). State of the Art: Zoombak tracks your dog, your car, even your children. NY Times, p. B1 of the New York Edition. Retrieved on Jan. 30, 2013 from: http://www.nytimes.com/2009/04/23/technology/personaltech/23pogue.html?pagewanted=a11&_r=0 (hereinafter "Zoombak").*

* cited by examiner

PET AND PEOPLE CARE MANAGEMENT SYSTEM

CROSS REFERENCE TO RELATED APPLICATION

This application claims the benefit under 35 U.S.C. §119 (e) of U.S. Provisional Patent Application No. 61/427,779, filed Dec. 28, 2010, the disclosure of which is hereby incorporated in its entirety.

FIELD OF THE INVENTION

The present invention relates generally to a pet and people care management system. Although the disclosure below is set forth in the context of pets, the care of people, including but not limited to the elderly or infirm, is also within the scope of the invention. More particularly, the invention relates to pet care providers who require access to the homes of individual clients to service and care for the clients' pets. It has particular application to pet services such as walking a client's pet dog during times when the client requests such services. Hereinafter, when mention is made of walking, it will be understood that this invention could relate generally to any service provided by a pet care company. Further, when reference is made to walking a dog, it will be understood that this invention could relate to walking any pet that a client desires.

BACKGROUND OF THE INVENTION

When a client signs up with a pet care company or specifically a dog walking service, the client must blindly trust that the pet care company will perform the services agreed upon. Therefore, there is a need to give the client the ability to check and make sure that the pet care company is providing the services that they promise.

Typically pet care providers come to an agreement with a client to arrive at a client's home at a specified time to walk the client's pet for a predetermined period of time or distance. Previously, there had been no way for a client to verify that the pet care provider was indeed arriving at the agreed upon time and walking the client's pet animal the contracted time or distance.

Therefore, it is an objective of the invention to give the client the ability to review exactly what time a pet care provider arrived and departed from the client's home, as well as viewing the length and path of the walk. Another important aspect of the invention is to create a mobile system utilizing smart phones to allow a pet care provider to scan in and scan out when visiting a client's home. This allows the pet care company and client to have real-time status updates to ensure that the client's pet is being taken care of.

Further, it is another object of the invention to simplify the process of scheduling a service appointment by allowing for online scheduling of the appointment.

SUMMARY OF THE INVENTION

In one aspect of the present invention, a pet and human care management system is provided. The system includes a portable electronic device including a microprocessor, a memory, a geographic location sensing mechanism, and a code input mechanism. A typical example of a portable electronic device suitable for purposes of the invention is a smartphone, but the device may also take the form of a pocket PC, tablet, PDA, for example. The microprocessor is programmed with instructions to input and store data logging the details of a care visit, especially a care visit that involves travel during the visit, such as a dog walking appointment or an appointment to accompany an elderly or disabled person in a shopping trip, for example. The programming includes an instruction to receive a customer code input by a user to identify a care customer. Preferably, the code is input automatically by using the portable device to scan a bar code or other image or object located at the site of the care customer, which may typically be the care customer's home. If scanning (or other form of automatic code entry) fails for any reason, the system preferably includes a database of customer names which a care provider can access remotely via the portable electronic device and select the appropriate customer from a list to check in, in lieu of scanning. Additionally or alternatively, an alphanumeric or similar written code may also be present at the care visit site as a backup, which may be entered manually into the portable device by the care provider. Once the code is scanned or otherwise entered, the portable device preferably automatically transmits the code to a server via a system website for verification. The programming also includes an instruction to receive input from the user to mark the start of a care visit to the care customer. This may consist simply of scanning/entering the customer code itself and the server confirming the code, or it may entail receiving a separate input from the caregiver such as the push of a button or entering of a separate code. The microprocessor is also programmed to cause to be stored the time at which the visit start input is received. This may be done by recording and storing the time locally if the device includes a clock, by immediately transmitting a visit start message to the server which includes a clock. More preferably, the time is logged both locally by the portable device and remotely by the server, so that in case the portable device does not have a signal when the start input is entered, the correct start time may still be stored and transmitted to the server later. The microprocessor is also programmed to cause to be stored the sensed geographic location of the portable device at a plurality of times during the care visit. These time-sequenced geographic data points may then be constructed into the path of the walk, shopping trip, or other ambulatory service provided by the caregiver during the care visit, again either locally by the portable device, remotely by the server, or both. Finally, the microprocessor is programmed to receive input from the user to mark the end of the care visit. Like the visit start input, the visit end input may also be the scanning/input of the customer code itself, some other input, or both. The time at which the visit end input is received is stored in a similar manner to the start time.

In one embodiment, the system includes a portable device that may be carried by the care customer. For example, when the care customer is a pet, this may be an electronic device attached to a collar worn by the pet. The pet-carried device may be programmed to be used in addition to or instead of a caregiver-carried device for any of the portable device functions, especially the location-logging function, as one of the pet owner's concerns will be whether the pet itself has actually walked the recorded route.

In another aspect of the present invention, a method of providing managed care to a pet or human customer is provided. The method includes providing a portable electronic device substantially as described above, scanning/entering the customer code at the care visit site, inputting care visit start data, transporting the device while providing an ambulatory service to the care customer so that the device records the path traveled, and inputting care visit end data.

In another aspect of the present invention, a pet and human care management system comprises a server and website programmed/constructed to facilitate the administration of care visits where the above-described portable devices are used. The server includes a microprocessor, a memory, and means for receiving data input. The system also includes a display that is either part of the server or configured to display information received from the server either directly or indirectly, such as the computer monitor of a customer or pet care company employee who logs into the website. The memory stores codes identifying care customers, and the microprocessor is programmed with instructions to input a received care customer code and compare the received care customer code to the stored care customer code. If the received care customer code equals the stored care customer code, the microprocessor is programmed to store a care visit start time, input a received care visit end message, store a care visit end time, input received data indicating the geographic location of a portable electronic device at a plurality of times between the care visit start time and the care visit end time, and display on the display the care visit start time, care visit end time, and input geographic locations of the portable electronic device. The microprocessor may be further programmed to automatically email a care customer a notification of the visit. A summary of the visit, including the start time, end time, and path traveled, may be either made available on website 70 for the customer to view or included in or attached to the email itself.

A method of administrating a care visit to a pet or human customer is also provided. The method includes providing a system including the above described server, causing the server to receive data from a portable device carried along the path of a care visit, and causing to be displayed on a display the start time, path, and end time of the care visit.

BRIEF DESCRIPTION OF THE DRAWINGS

It shall be understood that the drawings briefly described as follows are intended only to aid in illustrating certain embodiments of the invention, and the invention is not limited to the precise arrangements and instrumentalities shown in the drawings.

Referring to the drawings in detail, wherein like numerals indicate like elements throughout, there is shown in FIGS. 1-6, a preferred embodiment of a home check-in system in accordance with the present invention.

DETAILED DESCRIPTION OF THE PREFERRED EMBODIMENT

Figure 1:
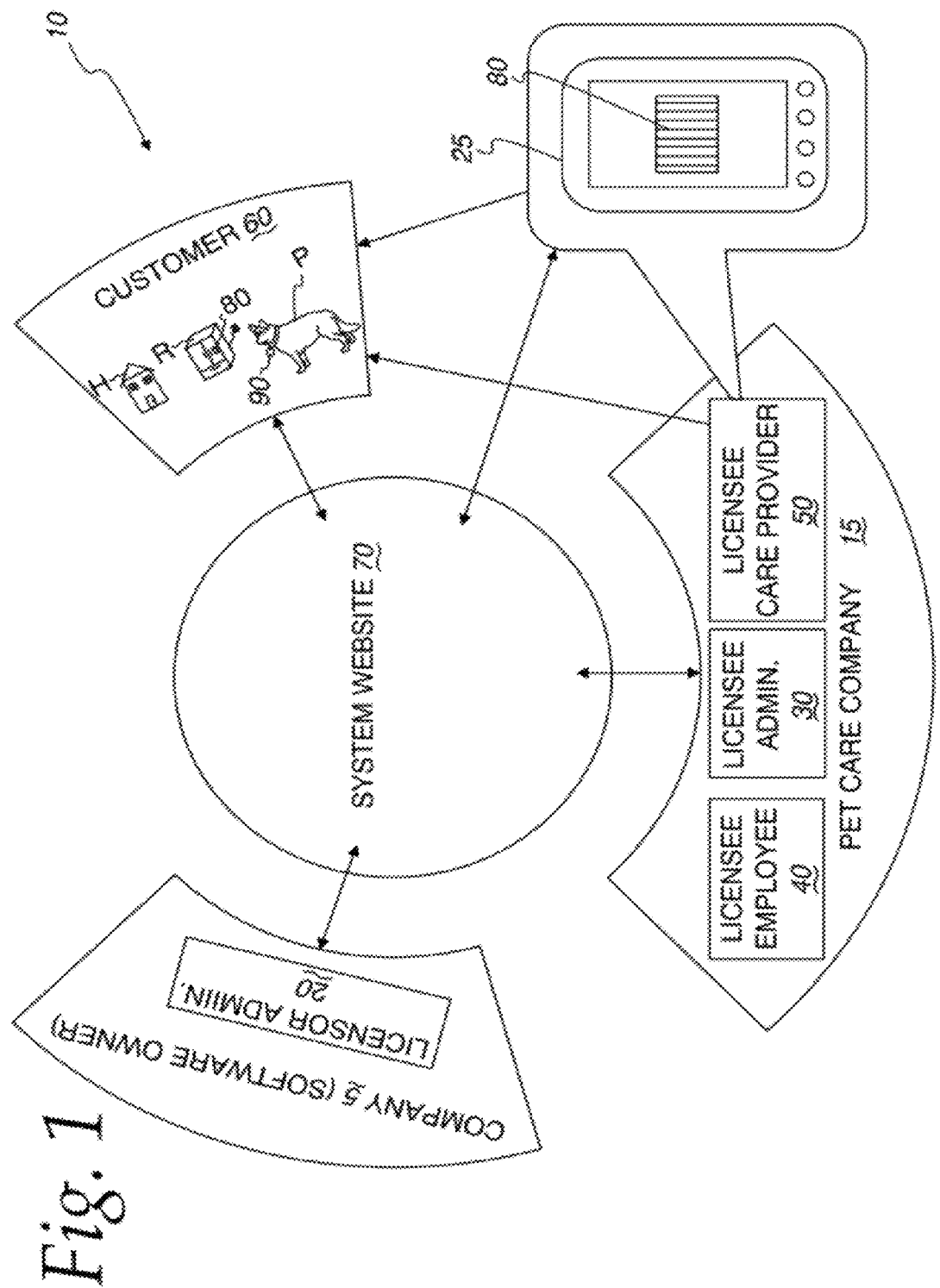
FIG. 1 represents a schematic diagram of one embodiment of a pet care management system according to the present invention, illustrating how various entities and devices relate to one another through use of the system.

A pet care management system 10 is a complete software and mobile application system for arranging, scheduling, and verifying pet care service visits. In the example illustrated herein, system 10 is configured for use between a licensor administrator 20 of a software owner company 5; a licensee administrator 30, a licensee employee 40, and a licensee care provider 50 of a pet care company 15; and a customer 60 having a home H where a pet care service visit takes place in an illustrated embodiment. However, the illustrated network of entities is intended merely as a non-limiting example of a particular embodiment facilitating what the inventor considers to be a typical pet care business model. Accordingly, it will be understood that the present invention does not require the participation of licensor administrator 20, licensee administrator 30, licensee employee 40 and licensee care provider 50 as separate entities; rather, these roles may be filled by as few as one entity, or even one person, without departing from the scope of the invention. Of course, in the case that software company 5 and pet care company 15 are the same entity or person, licensing the software of system 10 to pet care company 15 is not necessary, and the designations "licensor" and "licensee" referred to herein may be ignored, as well as any description of company 5 licensing any part of system 10 to company 15 or overseeing the use of system 10 by company 15.

Turning now to FIG. 1, system 10 uses an online website 70 to allow for pet care companies 15 to request a license from a company 5. Website 70 also allows for online scheduling of service appointments and customer billing of services. It will be understood that wherever the term "website" is used herein, whether indicating "website 70" or otherwise, it may refer to a single website or as many plural websites as may be desired for the described purpose.

System 10 also uses smartphones 25 with a customized mobile application that works on a variety of smartphone platforms. As depicted in FIG. 1, this mobile application allows a licensee care provider 50 to check in and out of customer home 60 using a photographic scanner, laser scanner, or other suitable bar code input device on smartphone 25 and a barcode 80 placed inside customer home 60. It will be understood that any suitable code input mechanism and corresponding code format are also within the scope of the invention, including but not limited to an RFID reader and emitter; a manual keypad and a printed code; and a magnetic strip reader and a magnetic strip; to name but a few possible pairings. In the situation where the walking of a pet is requested, an internal GPS (or other suitable location sensing mechanism, such as one that triangulates the position of smartphone 25 using cellular towers as opposed to GPS satellites) of smartphone 25 is used to track the time, distance and path that a care provider 50 has taken a pet during their walk. Alternatively or in addition to using smartphone 25 to track the details of the walk, a separate location sensing device 90, worn or carried by a pet P to be walked as shown in FIG. 1, may record the walk data, as an added safeguard against care provider 50 staging a fake walk without actually taking pet P, for example. Simultaneously using separate location sensing devices carried by care provider 50 and pet P may have the added benefit of confirming whether care provider 50 has remained with pet P during the walk as opposed to, for example, leaving pet P unattended for a significant amount of time while shopping in a store. As desired, device 90 may transmit the walk data to website 70, as the data is generated in real time or at the end of the walk, or it may simply store the data for later retrieval or viewing by customer 60.

Figure 2:
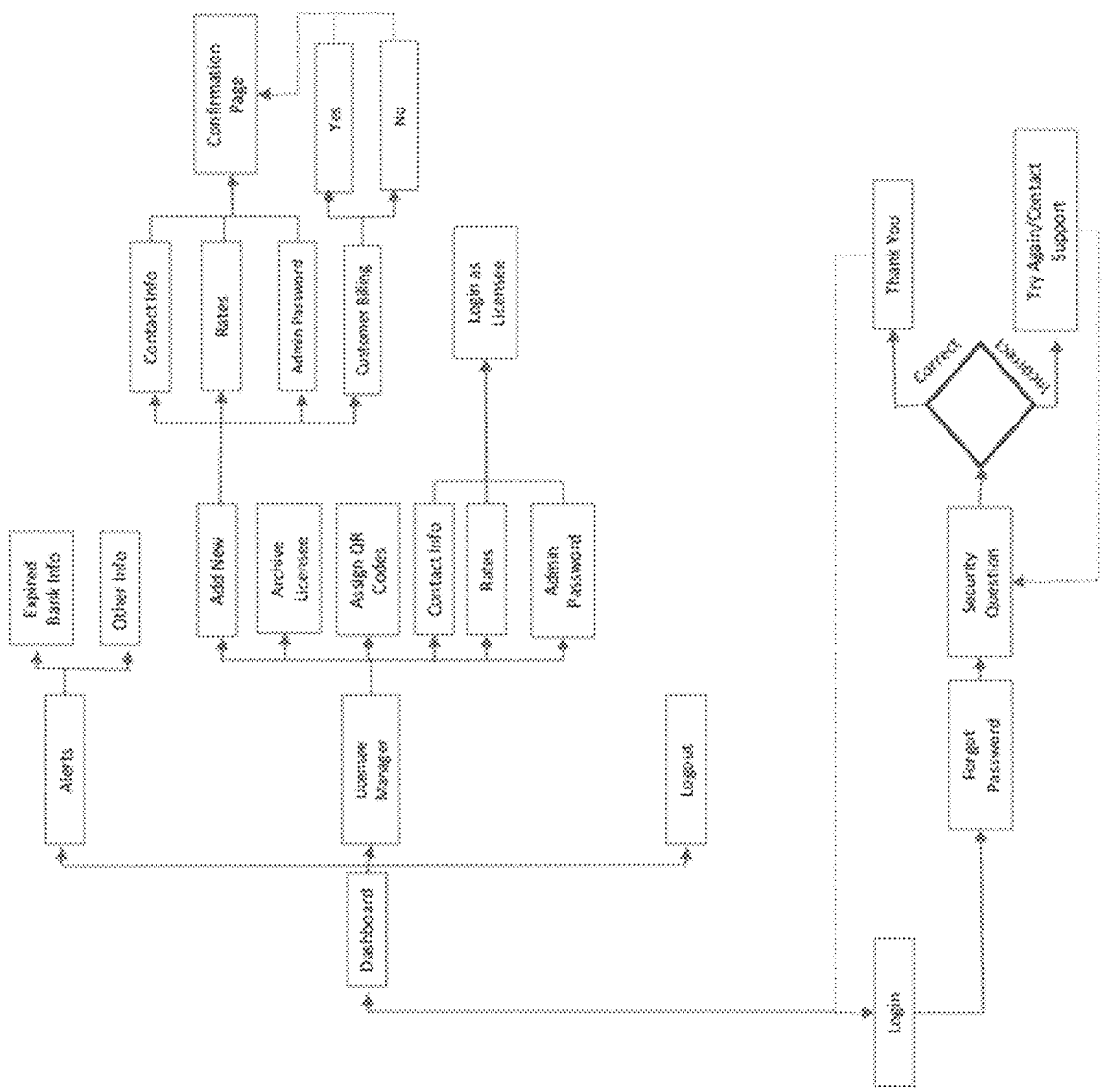
FIG. 2 represents a diagram of the home check-in system as applied to a licensor administrator.

Licensor administrator 20 is defined as an employee for company 5, which owns the software of system 10 and licenses the software out to individual pet care companies 15. Licensor administrator 20 has rights over website 70 of system 10 and end users who are registered with website 70. The use of system 10 by licensor administrator 20 is illustrated as a flowchart in FIG. 2.

Figure 3:
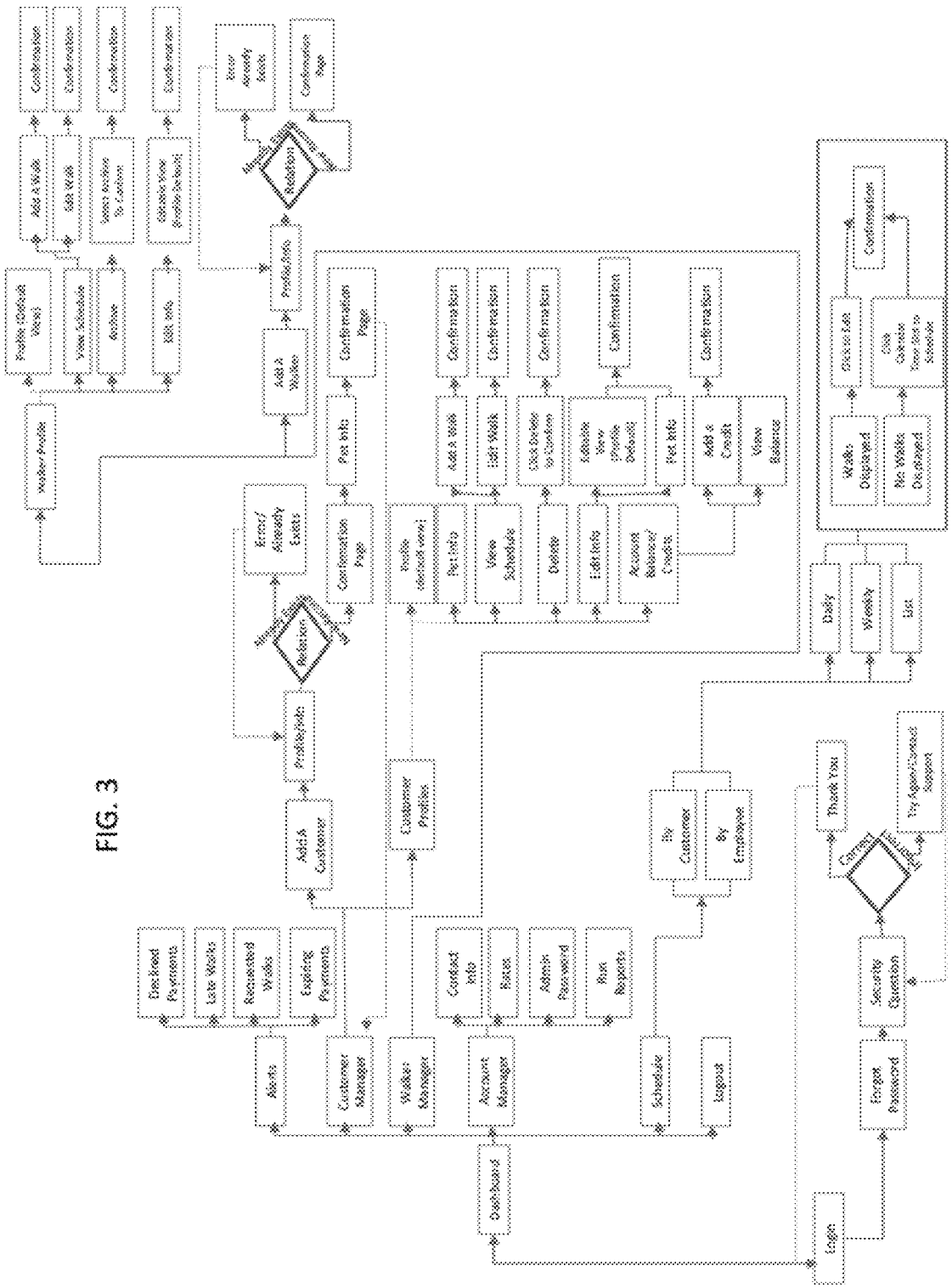
FIG. 3 represents a diagram of the home check-in system as applied to a licensee administrator.

Licensee administrator 30 is defined as the owner or senior manager of a pet care company 15 who has licensed system 10. Licensee administrator 30 has administrative rights to schedule pet care services, manage customers 60, maintain accounts of licensee care provider 50, utilize the licensor billing system for their customers and manage company 15 on system 10. The use of system 10 by licensee administrator 30 is illustrated as a flowchart in FIG. 3.

Figure 4:
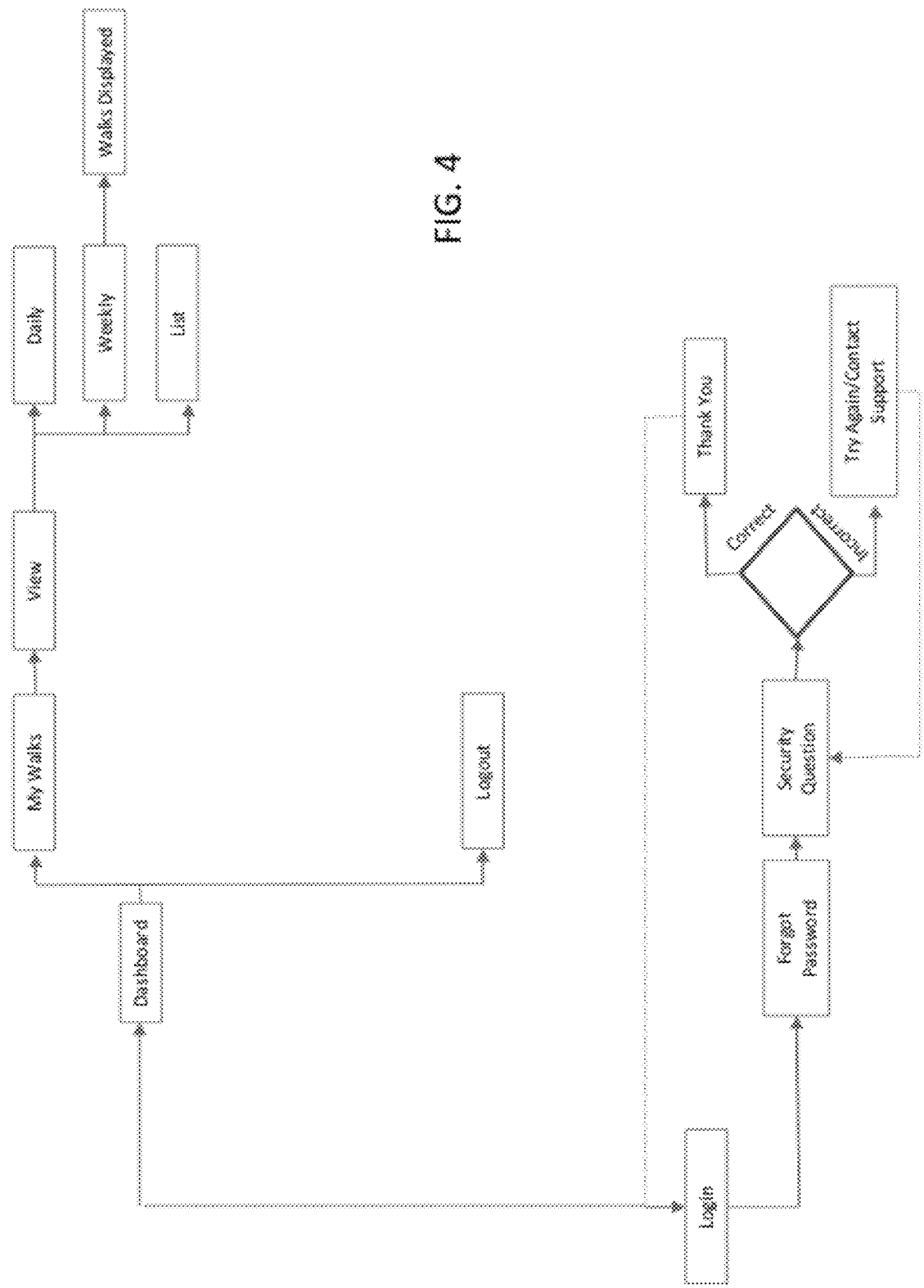
FIG. 4 represents a diagram of the home check-in system as applied to a licensee employee.

Licensee employee 40 is defined as an employee for pet care company 15. Licensee employee 40 has administrative rights to schedule walks, manage customers 60 and accounts of licensee care provider 50, and manage company 15 on system 10. Licensee employee 40 can add additional licensee care providers 50 and customers 60 but cannot add other licensee administrators 30. The use of system 10 by licensee employee 40 is illustrated as a flowchart in FIG. 4.

Figure 5:
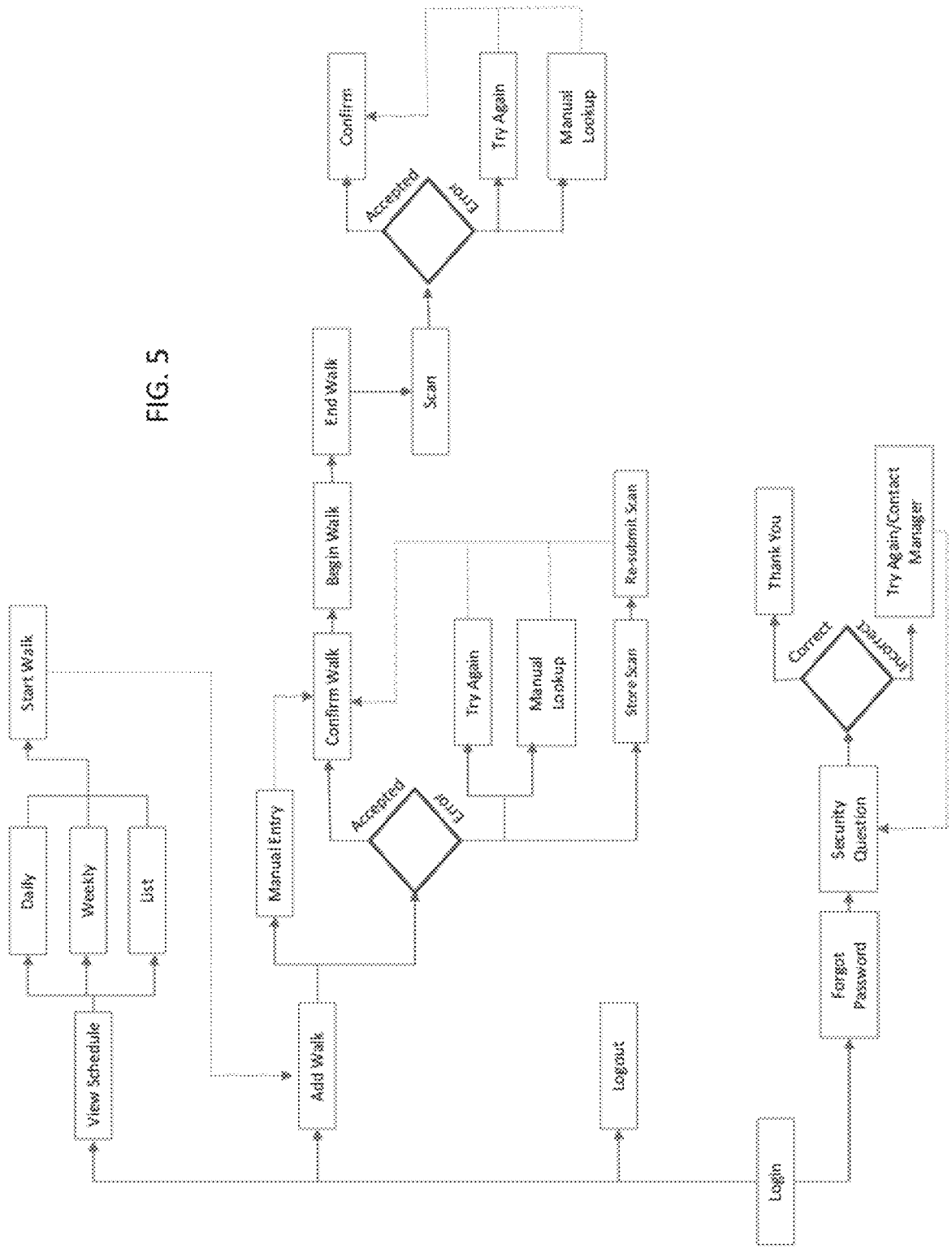
FIG. 5 represents a diagram of the home check-in system as applied to a licensee care provider.

Licensee care provider 50 is defined as a care provider or walker for a pet care company 15. Care provider 50 has access to specific rights related to pet care services and the mobile application. Care provider 50 also has access to an online calendar which displays their assigned customer walks. This calendar display can show either a daily, weekly or monthly overview of their scheduled appointments. The use of system 10 by licensee care provider 50 is illustrated as a flowchart in FIG. 5.

Figure 6:
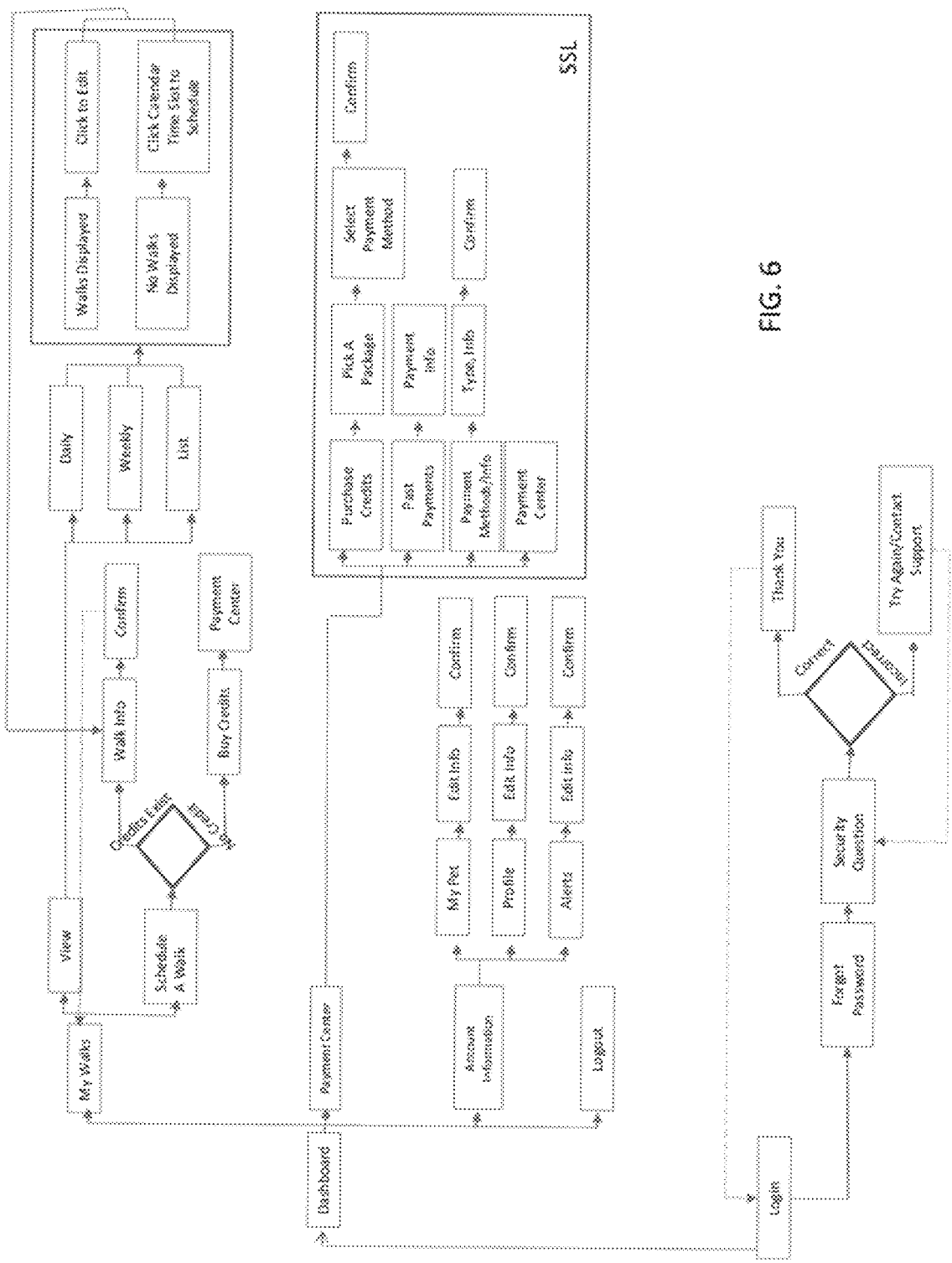
FIG. 6 represents a diagram of the home check-in system as applied to a customer.

Customer 60 is defined as any customer for pet care company 15. Customer 60 has access to a particular webpage within website 70 of system 10 that is dedicated only to their pet care company 15. Customer 60 has the ability to access this pet care company's webpage to verify certain information provided to customer 60 once they log on. On this webpage, customer 60 can see information pertaining to customer 60, including, for example, a calendar displaying all of their scheduled pet care appointments, their address, phone number, and/or their pet information. Customer 60 can use the system to make scheduling requests for the service of their choice. The calendar can display either a daily, weekly or monthly overview. The use of system 10 by customer 60 is illustrated as a flowchart in FIG. 6.

Licensee administrator 30 and licensee employee 40 are typically the senior decision makers within pet care company 15. They are typically tasked with the authority to manage dog walking operations and scheduling customers 60 online. Within system 10, licensee administrators 30 and licensee employees 40 will typically see the same webpage screens and have most of the same user permissions when they log on. However, only licensee administrator 30 has the authority to add, edit or archive licensee employees 40 and view or edit company account information.

Administrator 30 or employee 40 can also add or edit a care provider 50 or customer 60. They also have the ability to view schedules of all licensee care providers 50 and can run various reports containing details of each scheduled pet care appointment. System 10 also gives these users the ability to manage account settings. However, only licensee administrator 30 is given this user privilege. Licensee administrator 30 alone has the authority to manage their business account within system 10. From the main control panel, administrator 30 can click an "Account Manager" link which will allow them to do the following, for example: add or change their company logo, add or edit company contact information and hours of operation, change password information, view monthly billing statements from company 5, edit customer payment information, edit pet walk length, set up alerts for missed appointments, or order additional equipment.

In the illustrated embodiment, in order to use system 10, a pet care company 15 must first contact company 5 for a license to use system 10. This can be accomplished through website 70 of company 5 which has a specific page dedicated to allowing a pet care company 15 to apply for a license. Licensor administrator 20 is in charge of accepting or denying a licensee request and setting up a new licensee account.

A licensee request form asks a pet care company to leave contact information and set up their billing type to be either credit based on transaction based. A credit based billing type sets up a defined quantity of pet care service appointments up front and allows the licensee the option to obtain bulk discounts. A transaction based billing type will bill licensee 15 and customer 60 every week and clients are billed based on actual walks completed. There is also the option to include additional services such as walking a second pet, feeding the pet, watering plants, house sitting, transportation of pets, giving pets medication and working during off hours such as weekends and holidays.

Whether licensor administrator 20 accepts or rejects a request for license, an account is set up regardless for potential customer 15 and a custom URL website is created on website 70 of system 10. However, whether licensor administrator 20 actually accepts or rejects a request will determine whether the URL and account are marked active or inactive respectively. If administrator 20 rejects the request for license, then the account will be held inactive indefinitely until it is changed to an active state. Administrator 20 has the authority to edit the status of the account along with several other fields. The only field that administrator 20 cannot edit on an account is the transaction based billing type information. This is not editable and a new account must be set up to change this setting.

If licensor administrator 20 accepts the license request, then pet care company 15 can begin using system and setting up appointments on system 10. In order to schedule an appointment with a licensee care provider 50, either licensee administrator 30 or licensee employee 40 must login with their own user identification name and password to gain access to website 70 of system 10. After entering website 70, licensee administrator 30 and employee 40 have the ability to schedule an appointment with a licensee care provider 50.

To schedule an appointment, the user must input the date of service, the name of licensee care provider 50 and the services desired by customer 60. In this particular embodiment, administrator 30 or employee 40 would input the length of time or distance that customer 60 desired for their pet to be walked. Also, the date of service field will be pre-populated with the current day's date. However, this date can be altered and additional days can be added using check boxes corresponding to each day of the week.

Administrator 30 or employee 40 would then assign the appointment to the desired customer 60. If the desired customer 60 is a preexisting client, then administrator 30 or employee 40 can search for that customer 60 by name and select the appropriate customer 60 that appears in the search results. However, if customer 60 is a new client, the user is given an option to create a new customer and they can manually enter information pertaining to customer 60 on a separate screen. This information could include a full name, address, phone number, email, emergency contact information, pet information, house alarm code, preferred length of time or distance for walk, veterinary contact information, pet medical information, pet birthday, the date the customer signed up, days of service, referral information, credit card information and any additional necessary notes relating to customer 60.

If desired, administrator 30 or employee 40 could also edit or archive an existing customer 60. Archiving an existing customer 60 is defined as deactivating an account that can later be reactivated. Editing or archiving customer 60 information is accomplished from the main control panel where a user 30, 40 can click on a button labeled "manage customers". There, a user 30, 40 can manually edit any information about customer 60. In order to archive or disable a customer account, a user 30, 40 would simply change their status from active to inactive.

Licensee administrator 30 or licensee employee 40 also has the option of managing licensee care providers 50. During the scheduling of an appointment, a user 30, 40 has the option to either select a preexisting care provider 50 or creating a new care provider 50 for the particular appointment. If a new care provider 50 is desired, the user can input information such as the care provider's full name, hiring date, date of birth, photograph, biography, work username, home address, phone number, email address, type of transportation, license plate number, emergency contact information, and any additional necessary notes. Further, this information can be edited at any time by administrator 30 or employee 40.

Once this information is input, administrator 30 or employee 40 clicks a button on the computer screen labeled "Save" to save the appointment. This automatically saves the appointment to the calendars of both care provider 50 and customer 60. An alert email can also be automatically sent to both care provider 50 and customer 60 detailing the scheduled appointment and particular details about the job. For care provider 50, they will be sent details about the name of customer 60, pet's name, address, walk time, walk length or any special notes concerning this account. For customer 60, they will be sent details about the name of care provider 50, walk start time, and generic cancellation information and contact phone number should they need to cancel the appointment.

Once an appointment has been scheduled, the designated licensee care provider 50 can log into their computer or portable device/smartphone 25 to view their calendar work week online. This information includes items such as a daily and weekly calendar views, walks presently scheduled with details such as customer name and address, pet name, walk start time, walk window or walk distance, and walks previously completed with information such as customer name and address, pet name, length of scheduled walk, length of actual recorded walk, link to recorded Global Positioning System ("GPS") path, and any additional notes.

Once the time for a scheduled appointment arrives, care provider 50 goes to home H of customer 60. In one embodiment, in order for a customer 60 to use system 10, they must use a proprietary system which uses barcode technology, mobile devices 25 and an online scheduling tool. When a customer 60 signs up to use system 10, a unique barcode 80 will be created and printed for the residence of customer 60. Barcode 80 will contain a unique identification code and will be printed on magnet strips or a sticker, for example, so that they can be placed on a refrigerator R or other convenient location that can be easily accessed by a care provider 50.

Once care provider 50 enters home H of customer 60, they check in using their smartphone 25 which has been equipped with a barcode scanner. This barcode scanner may either be integral to smartphone 25, as in a mobile scanning application that is loaded on smartphone 25, using a camera component of smartphone 25 to capture and scan an image of barcode 80 as depicted in FIG. 1, or the scanning equipment may be an external attachment. Care provider 50 opens a mobile application program on their phone which is part of system 10. The mobile application will request that the user login with a username and password. The login information is sent to website 70 of system 10 and checks user credentials in the database as well as user rights. If the user is recognized, the mobile application will allow the user access. While in the application, the user will never be logged out of the program. In other words, the user login will never time out.

Once in the mobile application program, care provider 50 locates and scans barcode 80 located inside the home H of customer 60. As depicted in FIG. 1, one suitable type of scanning mechanism for this purpose is a mobile smartphone application of the type that uses a photographic image of bar code 80 captured by a camera device of smartphone 25. If there is no mobile signal at the time of the scan, the mobile application will recognize this and a message will appear asking the care provider if they wish to store the scan to be resubmitted when mobile signal is restored. Once mobile signal is restored, the care provider will receive a message to resubmit the scan where it is treated as a successful scan and recognizes the scan at its original scan time rather than when the stored scan was resubmitted. If care provider 50 cannot find a barcode or if barcode 80 is damaged, care provider 50 can use the mobile application to look up and choose the appropriate customer in order to check in, which would replace the need to scan barcode 80. Alternatively, an alphanumeric code corresponding to customer 60 may be present at the home H of customer 60 as a backup for care provider 50 to enter manually into smartphone 25.

However, if care provider 50 is able to successfully locate barcode 80 and the scan is successful, the name of customer 60 will display on the screen of smartphone 25. A prompt will appear and ask care provider 50 to verify that customer 60 name displayed is correct customer 60. If the scan is not successful, an error message will display on the screen of smartphone 25 stating the number of attempts made and further requesting that the user please try again or look up customer 60.

However if the scan is successful and the correct customer 60 is shown, then care provider 50 selects "Yes" to the on-screen prompt. At this point, information such as account information of customer 60, identification of care provider 50 and scan date and scan time is preferably sent to website 70 of system 10 to check the database of system 10 for proper verification. If care provider 50 selects "No" because the wrong customer 60 account information is shown, then a message will display on the screen of smartphone 25 requesting that the user attempt to rescan barcode 80 or contact an administrator 30 for assistance.

If this information is verified, then further information such as the status of the walk and the start time and date are posted on the calendar for this particular appointment. An email is also sent to customer 60 to let them know that the walk has started. However, if the database cannot verify the information such as in a circumstance where a customer 60 requested a last minute service appointment and the appointment was not entered into system 10, then the mobile application will display a message that the current walk is unscheduled and ask the care provider 50 to verify that this is correct. If care provider 50 verifies this, then system 10 will alert either license administrator 30 or employee 40 or both that an unscheduled walk is occurring with the name of customer 60, the name of care provider 50, date and time recorded. The mobile application will also continue to make a record of the unscheduled walk with information similar to a scheduled walk.

Whether the walk is scheduled or unscheduled, once the walk begins, smartphone 25 will preferably begin sending GPS coordinates in real time at regular intervals to the database of system 10 for mapping and tracking purposes. The display on smartphone 25 of care provider 50 will show information such as a running time, a radio button to show the calendar of work of care provider 50, and a radio button which care provider 50 can activate to show that the service appointment is completed.

Once care provider 50 has finished with their service appointment, they re-enter customer home 60 and activate the radio button which signals that the service appointment is complete. For example this radio button can be labeled "End Service Appointment" or "End Walk". Preferably, once this button is clicked, the scanner of smartphone 25 is again activated and care provider 50 scans the bar code at customer home 60. If the scan is successful, information such as, for example, the name of customer 60, a visual map of the geographic coordinates of the walk, total time and distance walked will appear on the screen of smartphone 25. If there is no mobile signal at the time of the scan, the mobile application will recognize this and a message will appear asking the care provider if they wish to store the scan to be resubmitted when mobile signal is restored. Once mobile signal is restored, the care provider will receive a message to resubmit the scan where it is treated as a successful scan and recognizes the scan at its original scan time rather than when the stored scan was resubmitted. A text field is also available on the screen to allow care provider 50 to enter any notes about the walk.

A button will also appear after a successful scan which allows the user to submit their completed service appointment. Clicking on this button sends user information back to the database of system 10 for verification. If system 10 verifies the information, the status of the service appointment or walk is posted to the calendar including an update to the status stating that the appointment is complete, and sending the date and start and end time of the service appointment. An email is also sent to customer 60 to let them know that the walk has ended. At that time, smartphone 25 also stops sending GPS coordinates to system 10 and a final map displaying the walk path is displayed on website 70 of system 10 for the specific customer 60 to review.

While the invention has been described with respect to certain embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An appointment management system for a pet care visit including a walk for a pet care customer's pet, comprising:
    a pet caregiver portable electronic device including a portable electronic device microprocessor, a portable electronic device memory, and a geographic location sensing mechanism, wherein the pet caregiver portable electronic device is configured to receive data input and to determine its geographic location; and
    a server including a server processor, a server memory, and wherein the server is configured to receive data input, the server operating a website storing user accounts for the pet care customer and the pet caregiver, permitting the pet caregiver and the pet care customer to schedule the per care visit on the website, and automatically storing appointment information and making the appointment information accessible for viewing on the pet caregiver personal electronic device and an electronic device of the pet care customer, the appointment information indicating at least one of a distance, a duration, and a route of the walk for the scheduled visit;
    the server memory storing a code identifying the pet care customer and linked to information stored in the server memory identifying the customer's pet and a pet care appointment site at which the pet is located, and providing the caregiver access to the pet identifying information and the location of the pet care appointment site, as the pet caregiver logs into a user account of the pet caregiver on the website, and;
    an image of the pet care customer code stored at the pet care appointment site on a medium readable by the portable electronic device, to enable the pet caregiver portable electronic device to reed the code at the pet care appointment site when placed in proximity to the customer code medium; and
    the server programmed with instructions for the server processor to
    receive a transmission of the code initiated by the pet caregiver at a beginning of the pet care visit from the pet caregiver portable electronic device located at the pet care appointment site,
    compare the received code to the code identifying the pet care customer in the server,
    subject to at least one precondition coded into the instructions, said at least one precondition including that the received code equal the stored code, perform a storing and displaying subroutine including instructions to:
        store a pet care visit start time corresponding to a pet care visit start signal transmission from the pet caregiver portable electronic device, the start signal transmission initiated at the pet care visit start time from the pet care appointment site,
        store a pet care visit end time corresponding to a pet care visit end signal received from the pet caregiver portable electronic device, the end signal transmitted at the pet care visit end time from the pet care appointment site,
        store data received from the pet caregiver portable electronic device indicating time-sequenced geographic locations of the portable electronic device at a plurality of times, separated by regular intervals, between the pet care visit start time and the pet care visit end time, and
    in response to the end signal from the pet caregiver portable electronic device, transmit data to the electronic device of the pet care customer to permit display on a display of the pet care customer electronic device the pet care visit start time, the pet care visit end time, and a visual map of a walk path constructed from said time-sequenced geographic locations of the pet caregiver portable electronic device at each of said plurality of times, to permit the pet care customer to confirm at a route of the walk,
    the pet caregiver portable electronic device programmed with instructions for the pet caregiver portable electronic device microprocessor to record the geographic location of the pet caregiver portable electronic device at each of said plurality of times separated by the regular intervals and to transmit data representing said geographic location at each of said plurality of times to the server, and
    the pet caregiver portable electronic device further comprising a clock and being further programmed with instructions to
        detect whether a transmission signal is available to transmit the pet care visit start or end signal during the pet care visit start or and time, respectively; and
    if the transmission signal is unavailable,
        read and store the time from the clock when the input is received; and
        transmit the pet care visit start or end signal and the corresponding stored time from the clock to the server when the transmission signal is available.

2. The system of claim 1, said server memory further storing a database or at least one care provider login, the server further programmed with an instruction for the microprocessor to receive a care provider login transmitted from the portable electronic device, said at least one precondition on performing the storing and displaying subroutine further including that the received care provider login equal the stored care provider login.

3. The system of claim 1, said storing and displaying subroutine further including instructions to transmit to said pet care customer electronic device, for display on said pet care customer electronic device display, a representation of a total distance traveled by said portable electronic device between the pet care visit start time and the pet care visit end time.

4. The system of claim 1, wherein said making the appointment information accessible to the caregiver personal electronic device and the pet care customer electronic device includes an action selected from transmitting an email message to the respective caregiver or pet care customer, and generating and storing a representation of the appointment information accessible by the caregiver or pet care customer on the website within the respective user account.

\* \* \* \* \*

UNITED STATES PATENT AND TRADEMARK OFFICE
CERTIFICATE OF CORRECTION

PATENT NO. : 9,165,334 B2
APPLICATION NO. : 13/338021
DATED : October 20, 2015
INVENTOR(S) : Doug Simon Page 1 of 1

It is certified that error appears in the above-identified patent and that said Letters Patent is hereby corrected as shown below:

In the Claims

Claim 1, col. 9, line 58, delete "per" and insert therefor --pet--.

Claim 1, col. 10, line 9, delete "reed" and insert therefor --read--.

Signed and Sealed this
Ninth Day of August, 2016

Michelle K. Lee
*Director of the United States Patent and Trademark Office*